US012193812B2

(12) United States Patent
Mannheimer et al.

(10) Patent No.: US 12,193,812 B2
(45) Date of Patent: *Jan. 14, 2025

(54) SYSTEM AND METHOD FOR ROBUST PULSE OXIMETRY USING ASYMMETRIC DISTANCE-DEPENDENT CALIBRATION

(71) Applicant: Apple Inc., Cupertino, CA (US)

(72) Inventors: Paul D. Mannheimer, Los Altos, CA (US); Albert E. Cerussi, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,462

(22) Filed: Aug. 25, 2023

(65) Prior Publication Data

US 2024/0130648 A1 Apr. 25, 2024
US 2024/0225496 A9 Jul. 11, 2024

Related U.S. Application Data

(63) Continuation of application No. 17/018,739, filed on Sep. 11, 2020, now Pat. No. 11,771,350.

(51) Int. Cl.
*A61B 5/1455* (2006.01)
*A61B 5/00* (2006.01)

(52) U.S. Cl.
CPC ...... *A61B 5/14552* (2013.01); *A61B 5/14551* (2013.01); *A61B 5/681* (2013.01);
(Continued)

(58) Field of Classification Search
CPC . A61B 5/14552; A61B 5/14551; A61B 5/681; A61B 2560/0223; A61B 2562/0233
See application file for complete search history.

(56) References Cited

U.S. PATENT DOCUMENTS 5,922,607 A * 7/1999 Bernreuter ......... A61B 5/14551
436/805
6,421,549 B1 * 7/2002 Jacques ............. G01N 21/3151
600/323

(Continued)

OTHER PUBLICATIONS

Non-Final Office Action received for U.S. Appl. No. 17/018,739, mailed on Aug. 17, 2022, 11 pages.

(Continued)

*Primary Examiner* — Eric F Winakur
*Assistant Examiner* — Abid A Mustansir
(74) *Attorney, Agent, or Firm* — Kubota & Basol LLP

(57) ABSTRACT

Estimation of a characteristic of a user's physiological signals can be improved using one or more calibration relationships that may be dependent on a characteristic of the optical sensor. For example, different calibration relationships can be used that are dependent on a spatial characteristic and/or that are dependent on a wavelength characteristic of the light emitting component(s) of the respective emitter of a channel. In some examples, a unique calibration relationship can be used for each channel. In some examples, a common calibration relationship can be used for multiple channels with shared distance and/or wavelength characteristics. Utilizing distance-dependent and/or wavelength-dependent calibration relationships can improve robustness of pulse oximetry measurements.

23 Claims, 8 Drawing Sheets

(52) U.S. Cl.
CPC ................. *A61B 2560/0223* (2013.01); *A61B 2562/0233* (2013.01)

(56) References Cited

U.S. PATENT DOCUMENTS

| | | | |
|---|---|---|---|
| 7,142,901 B2 * | 11/2006 | Kiani ................. | A61B 5/14551 600/323 |
| 8,346,332 B2 | 1/2013 | Kuhn et al. | |
| 8,788,004 B2 | 7/2014 | Chen et al. | |
| 10,470,692 B2 | 11/2019 | Lange et al. | |
| 10,646,145 B2 | 5/2020 | Pekander et al. | |
| 2017/0325698 A1 * | 11/2017 | Allec .................... | A61B 5/721 |
| 2019/0246967 A1 * | 8/2019 | Pekander ........... | A61B 5/14552 |

OTHER PUBLICATIONS

Notice of Allowance received for U.S. Appl. No. 17/018,739, mailed on May 26, 2023, 9 pages.

* cited by examiner

SYSTEM AND METHOD FOR ROBUST PULSE OXIMETRY USING ASYMMETRIC DISTANCE-DEPENDENT CALIBRATION

CROSS-REFERENCE TO RELATED APPLICATIONS

This application is a continuation of U.S. application Ser. No. 17/018,739 filed Sep. 11, 2020, the content of which is herein incorporated by reference in its entirety for all purposes.

FIELD OF THE DISCLOSURE

This relates generally to pulse oximetry systems and methods, and more particularly, to pulse oximetry systems and methods utilizing asymmetric distance-dependent calibration to improve robustness of pulse oximetry measurements.

BACKGROUND OF THE DISCLOSURE

Information or characteristics (e.g., pulse rate or arterial oxygen saturation) of a user's physiological signals can be determined by pulse oximetry systems and methods. In a basic form, pulse oximetry systems and methods can utilize one or more light emitters to illuminate a user's tissue and one or more light detectors to receive light that enters and probes a subsurface volume of tissue. The light emitters and light detectors can be in contact with the tissue or can be remote (i.e., not in contact) to the tissue surface. For example, arterial oxygen saturation can be estimated based on a modulation ratio for two different wavelengths of light. However, the estimates of information or characteristics of a user's physiological signals may be inaccurate when the light emitters or light detectors are not in good contact, the light emitters or detectors are oriented differently with respect to the tissue surface than expected, there are other anomalies in the path of light from light emitters to light detectors, or under other conditions that results in measurements that are incompatible with assumptions of pulse oximetry.

SUMMARY OF THE DISCLOSURE

This relates to systems and methods for robust estimation of a characteristic of a user's physiological signals. For example, the physiological characteristic can be oxygen saturation of the hemoglobin in arterial blood (SaO2) as estimated by a pulse oximeter (SpO2). In some examples, an optical sensor may include multiple channels with asymmetries between respective emitters and detectors of the multiple channels. For example, the different distances between different emitter and detector pairs (e.g., asymmetric distances among the multiple channels) can result in asymmetric effective distances in the expected distributions of possible light paths between the different emitter and detector pairs. Additionally or alternatively, the placement of light emitting components within the light emitter (e.g., the position and/or angle of the light emitting components) may also result in asymmetric effective distances in the expected distributions of possible light paths among multiple channels (e.g., even among those channels with otherwise uniform separation between respective emitter and detector pairs). To improve accuracy of the estimation of a physiological characteristic (e.g., SpO2), different calibration relationships (e.g., modulation ratio R-to-SaO2 mappings) can be used that may be dependent on a characteristic of the optical sensor. For example, different calibration relationships can be used that are dependent on a spatial characteristic (e.g., distance between the respective emitter and respective detector of a channel, die position and/or angle) and/or that are dependent on a wavelength characteristic of the light emitting components of the respective emitter of a channel. In some examples, a unique calibration relationship can be used for each channel. In some examples, a common calibration relationship can be used for multiple channels with shared distance and/or wavelength characteristics. Utilizing asymmetric distance-dependent and/or wavelength-dependent calibration can improve robustness of pulse oximetry measurements (e.g., for improved accuracy of SpO2 estimates).

DETAILED DESCRIPTION

Figure 1A:
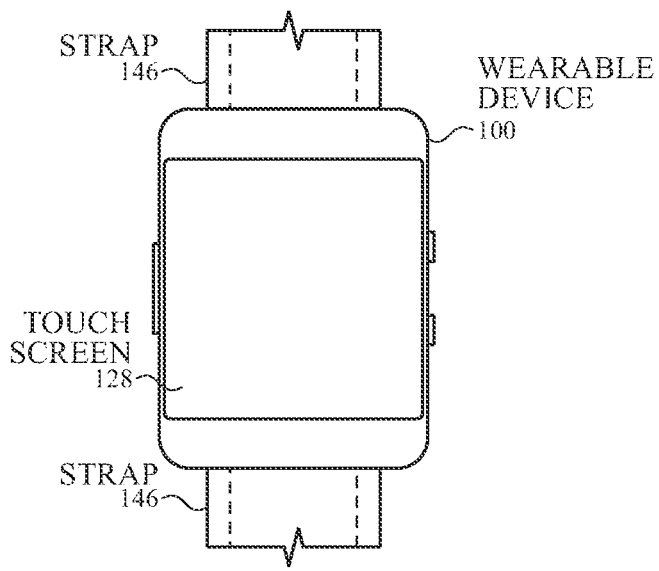
FIGS. 1A-1B illustrate views of an exemplary electronic device including one or more optical sensors according to examples of the disclosure.

In the following description of examples, reference is made to the accompanying drawings which form a part hereof, and in which it is shown by way of illustration specific examples that are optionally practiced. It is to be understood that other examples are optionally used and structural changes are optionally made without departing from the scope of the disclosed examples.

This relates to systems and methods for robust estimation of a physiological characteristic (e.g., arterial blood oxygen saturation) using a user's physiological signals. As used herein, physiological signals refer to signals generated by a physiological sensor (e.g., a photoplethysmogram (PPG) signal) that can be used for estimating the physiological characteristic (or condition) of a patient or user. A user's physiological signals can be determined by measurements using pulse oximetry systems. Such pulse oximetry systems can be designed to be sensitive to changes in the red blood cell number/concentration, volume, or blood oxygen state included in the sample or a user's vasculature. In a basic form, pulse oximetry systems can employ a light emitter (or plurality thereof) that injects light into the user's tissue and a light detector (or plurality thereof) to receive light that reflects and/or scatters and exits the tissue. In some examples, at least a portion of the photon path length interacts with tissue subsurface structures. Pulse oximetry systems can include, but are not limited to, arterial blood oxygen saturation estimation systems (SpO2 systems) configured to capture optical signals such as PPG signals. SpO2 systems can estimate a characteristic of physiological signals based on the attenuation of light (as measured by a physiological signal sensor) that varies over the duration of the cardiac cycle. Attenuation can be due to absorption, and/or scattering resulting from physiological/mechanical changes. Physiological/mechanical changes can include, but are not limited to, red blood cell number, cell/blood volume, red blood cell orientation, red blood cell/blood velocity, shear force, location/spatial distribution, concentration in the tissue, or other tissue properties (e.g., hydration, etc.), or a combination thereof. The estimated characteristics of the physiological signals (e.g., derive from the PPG signals) can include SpO2, heart rate, etc.

In some examples, an optical sensor may include multiple channels with asymmetries between respective emitters and detectors of the multiple channels. For example, the different distances between different emitter and detector pairs (e.g., asymmetric distances among the multiple channels) can result in asymmetric effective distances in the expected distributions of possible light paths between the different emitter and detector pairs. It should be understood that the asymmetries described herein refer to differences in characteristics between two channels, rather than the symmetry/asymmetry of the overall layout of emitters and detectors (e.g., such as in the symmetric layouts of emitters and detectors in FIGS. 1B, 1D and 1E on the underside of wearable device 100). Additionally or alternatively, the placement of light emitting components within the light emitter (e.g., the position and/or angle of the light emitting components) may also result in asymmetric effective distances in the expected distributions of possible light paths among multiple channels (e.g., even among those channels with otherwise uniform separation between respective emitter and detector pairs). To improve accuracy of the estimation of a physiological characteristic (e.g., SpO2), different calibration relationships (e.g., modulation ratio R-to-SaO2 mappings) can be used that may be dependent on a characteristic of the optical sensor. For example, different calibration relationships can be used that are dependent on a spatial characteristic (e.g., distance between the respective emitter and respective detector of a channel, die position and/or angle) and/or that are dependent on a wavelength characteristic of the light emitting components of the respective emitter of a channel. In some examples, a unique calibration relationship can be used for each channel. In some examples, a common calibration relationship can be used for multiple channels with shared distance and/or wavelength characteristics. Utilizing asymmetric distance-dependent and/or wavelength-dependent calibration can improve robustness of pulse oximetry measurements (e.g., for improved accuracy of SpO2 estimates).

Figure 1C:
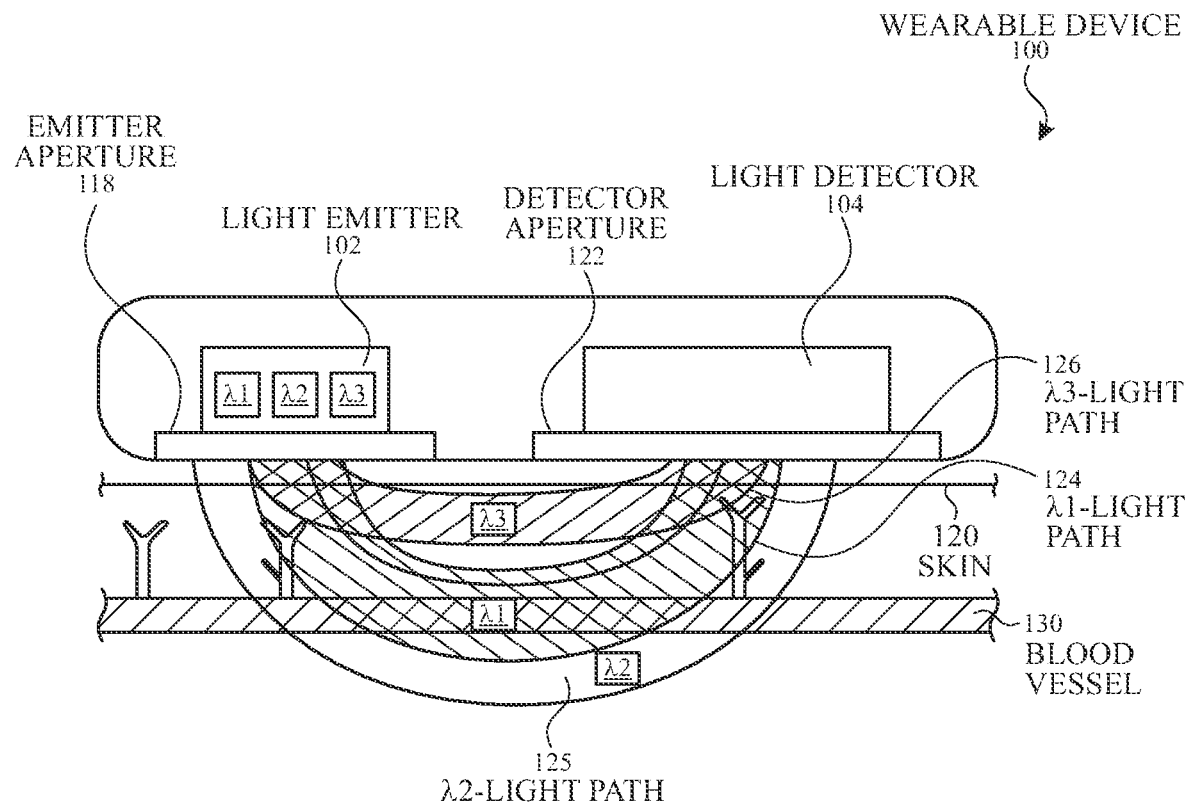
FIG. 1C illustrates a cross-sectional view of exemplary wearable device including one or more light emitters and one or more light detectors according to examples of the disclosure.
Figure 1B:
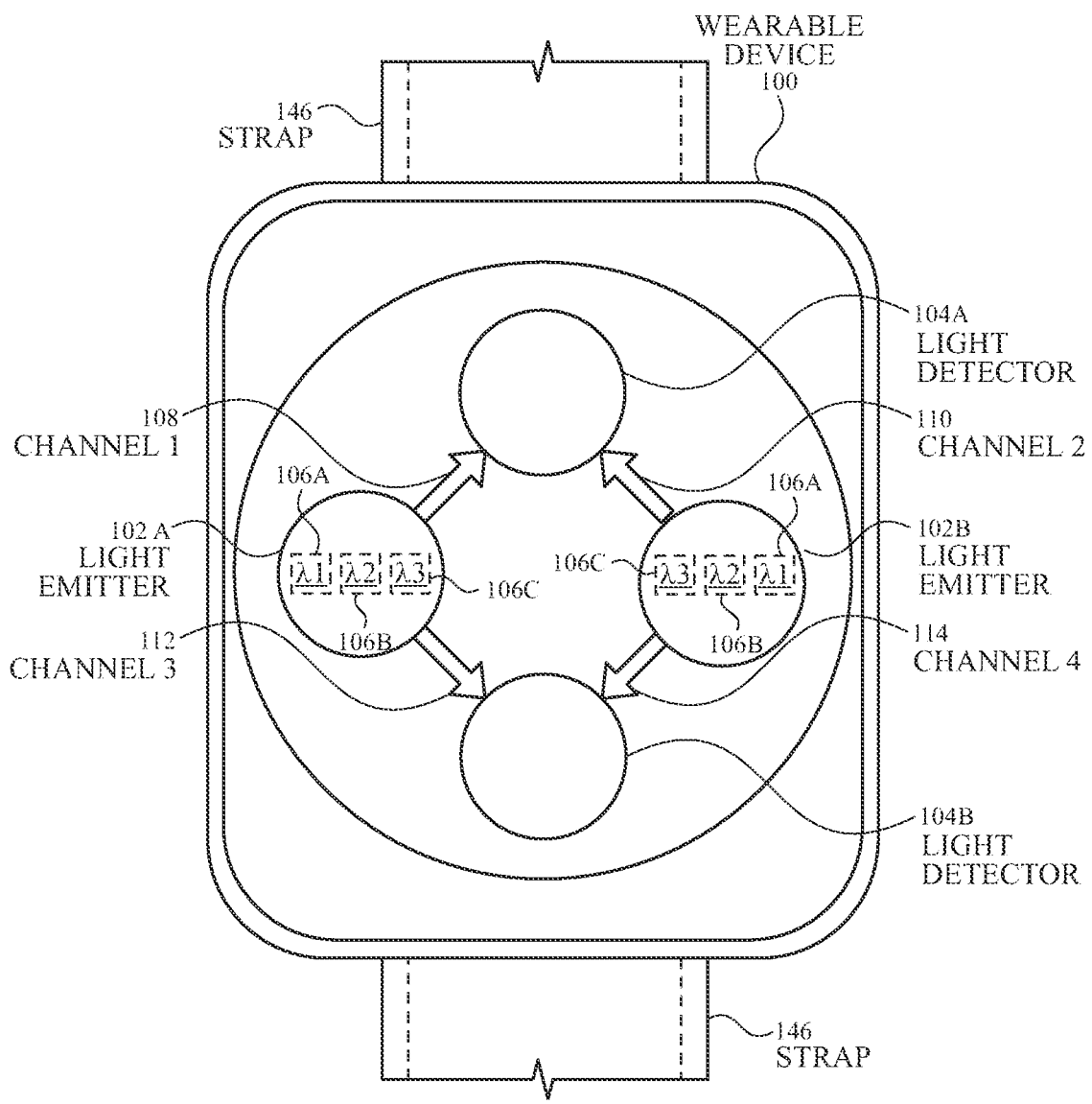

FIGS. 1A-1B illustrate views of an exemplary electronic device including one or more optical sensors according to examples of the disclosure. FIG. 1A illustrates a top view of an exemplary wearable device 100 that can include a touch screen 128 and can be attached to a user using a strap 146 or other fastener. FIG. 1B illustrates a bottom view (underside) of exemplary wearable device 100 including one or more optical sensors comprising one or more light emitters and one or more light detectors according to examples of the disclosure. For example, FIG. 1B illustrates device 100 that can include light emitters 102A-102B and light detectors 104A-104B. Device 100 can be positioned such that light emitters 102A-102B and light detectors 104A-104B are proximate to a user's skin or any other tissue site. For example, device 100 can be held in the user's hand or strapped to the user's wrist, among other possibilities. In some examples, light emitters 102A-102B and light detectors 104A-104B can be in close proximity (e.g., within a threshold distance, such as 5 mm, for example) to the surface of user's skin or can be physically contacting a surface of user's skin, which can reduce the amount of detected light that has not traveled through tissue.

As described herein, each light emitter represents a unique location on the device at which light can be emitted from device, and each light detector represents a unique location on the device at which the device can collect light. The light emitters and light detectors can preferably be optically isolated within the device such that emitted light from an emitter exits the device before being sensed by a detector. As described herein, light emitters can be configured to emit light at a plurality of wavelengths (e.g., at least two wavelengths for SpO2 measurements).

In some examples, each of light emitters 102A-102B can include one or more light emitting components to generate light at different wavelengths. For example, FIG. 1B illustrates each light emitter 102A-102B including three discrete light emitting components 106A-106C (e.g., light emitting diodes (LEDs) or organic light emitting diodes (OLEDs)) configured to generate light at multiple wavelengths including at least wavelengths $\lambda 1$, $\lambda 2$, and $\lambda 3$, respectively. Although three wavelengths are shown, in some examples, device 100 may include light emitting components at fewer or more wavelengths. Additionally, in some examples, each light emitter can include one light emitting component with a tunable wavelength (e.g., voltage or current controlled) or with different filters, rather than using a different light emitting component for each wavelength. In some examples, each light emitter 102A-102B can be optically coupled to each light detector 104A-104B for each wavelength. For example, light emitter 102A can be optically coupled to both light detectors 104A-104B and light emitter 102B can be optically coupled to both light detectors 104A-104B. Light emitter 102A can be configured to emit light (at one or more wavelengths) and detected by light detector 104A and detected by light detector 104B. Light emitter 102B can also be configured to emit light (at one or more wavelengths) detected by light detector 104A and detected by light detector 104B. As illustrated in FIG. 1B, a first channel 108 can be used to measure signal at light detector 104A from light emitter 102A (at each respective wavelength), a second channel 110 can be used to measure signal at light detector 104A from light emitter 102B (at each respective wavelength), a third channel 112 can be used to measure signal at light detector 104B from light emitter 102A (at each respective wavelength), and a fourth channel 114 can be used to measure signal at light detector 104B from light emitter 102B (at each respective wavelength). The measured signal at each detector can include light measured from various light paths (e.g., expected distributions of possible light paths through the skin and/or air) between the respective emitter and detector of the channel.

Device 100 can also include processing circuitry to process light detected from light detectors 104A-104B. In some examples, the processing circuitry can be used to determine the user's physiological signals and extract information (e.g., one or more characteristics) from the physiological signals. In some examples, a physiological characteristic can be one or more measures of heart rate or a hemoglobin oxygen saturation level (e.g., an arterial oxygen saturation (SpO2)). In some examples, the processing circuitry can remove or reduce motion artifacts from the physiological signals to account for non-cardiac-induced pulsatile blood volume changes. In some examples, the processing circuitry can process light detected from light detectors 104A-104B for functions independent from determining the user's physiological signals.

FIG. 1C illustrates a cross-sectional view of exemplary wearable device 100 including one or more light emitters and one or more light detectors according to examples of the disclosure. As illustrated in FIG. 1C, light emitter 102 can generate light at one or more wavelengths that can exit device 100 at emitter aperture 118 (e.g., a window). The light can be directed towards, and incident upon, the user's skin 120 and some of the light can be returned back toward device 100 (e.g., reflected and/or scattered from interacting with the skin). The light can reenter device through detector aperture 122 (e.g., a window) and be detected by light detector 104. A portion of light can be absorbed by molecules in skin 120, vasculature, and/or blood. Pulsatile blood flow in the user can lead to changes in the arterial vessel diameters, tissue hemoglobin concentration or volume, red blood cell orientation, velocity, or other physical states during a pressure change (e.g., diastole to systole), which can be included in light (e.g., via a scattering or absorption contrast mechanism) within the field of view of light detector 104. In some examples, heart rate can be estimated based on the changes in the detected light at one or more wavelengths due to pulsatile blood flow. In some examples, oxygen saturation in the blood can be estimated based on a ratio between physiological signal measurements (e.g., light intensity signals at light detectors) at two (or more) wavelengths. For example, oxygen saturation can be estimated based on a relative modulation ratio at two or more wavelengths. In some examples, the modulation ratio can be a perfusion index (PI) ratio based on physiological signal measurements at two or more wavelengths. Although the intensity of the physiological signal (or more generally the magnitude of each independent wavelength measurement) may change due to variations in the pulsations of blood, movement and the heterogeneity of tissue, the relative modulation ratio (e.g., between red light and infrared light) can be relatively stable indicator of oxygen saturation (e.g., via an empirical mapping between the relative modulation ratio and oxygen saturation).

In some examples, the signals from the one or more light emitters and one or more light detectors can be utilized to perform other functions aside from measuring the user's physiological signals and extracting information/characteristics from the physiological signals. For example, one or more light emitters and one or more light detectors can be configured for monitoring whether or not the device remains in contact with a user's skin (e.g., on-wrist and/or off-wrist detection) and/or whether the device is in contact with a non-skin surface such as a table.

FIG. 1C illustrates exemplary light paths for three different wavelengths $\lambda 1$, $\lambda 2$ and $\lambda 3$. Light path 124 can correspond to expected distributions of possible light paths at wavelength $\lambda 1$ (e.g., in the wavelength range of 620 nm-750 nm) and light path 125 can correspond to expected distributions of possible light paths at wavelength $\lambda 2$ (e.g., in the wavelength range of 750 nm-1400 nm). In some examples, wavelength $\lambda 1$ can be in the range of visible light (e.g., 400 nm-700 nm) and wavelength $\lambda 2$ can be in the range of near-infrared (NIR) light (e.g., 700-1100 nm), which can be strongly absorbed by blood and other molecules in the user's tissue and blood. In some examples, wavelength $\lambda 1$ can be red light and wavelength $\lambda 2$ can be IR light. Light path 126 can correspond to expected distributions of possible light paths at wavelength $\lambda 3$ (e.g., in the wavelength range of 495 nm-570 nm). In some examples, $\lambda 3$ can be in a lower wavelength range of visible light (e.g., 400 nm-495 nm), such as blue light, or near ultraviolet light (e.g., 300 nm-400 nm), or other portions of the visible light, NIR, short-wave IR spectra. It should be understood that these wavelength ranges are for exemplary purposes and different wavelength ranges are possible for $\lambda 1$, $\lambda 2$, and $\lambda 3$ (or any additional wavelengths). In some examples, the light at multiple wavelengths from the multiple light emitting components of an emitter exiting the device can preferably partially or fully overlap (e.g., light paths 124-126 can be partially or fully overlapping). As shown in FIG. 1C, in some examples, different wavelengths can penetrate different depths within skin 120. For example, light paths 124 and 125 corresponding to wavelengths $\lambda 1$ and $\lambda 2$ can penetrate more deeply within the skin 120 and underlying tissue, whereas light path 126 corresponding to wavelength $\lambda 3$ can penetrate less deeply within skin 120 and the underlying tissue. Additionally, although the light paths may penetrate different depths, it is understood that light at some wavelengths can penetrate a variety of depths including shallower and deeper within the tissue.

Skin 120 and underlying tissue can include the blood vessels (arterial and venous) such as blood vessel 130. Light emitter 102 and light sensor 104 can be located and wavelengths can be selected such that light paths 124 and 125 corresponding to wavelengths $\lambda 1$ and $\lambda 2$ can be sensitive to arterial blood volume changes to enable an estimation of the characteristic of a user's physiological signals.

Figure 1D:
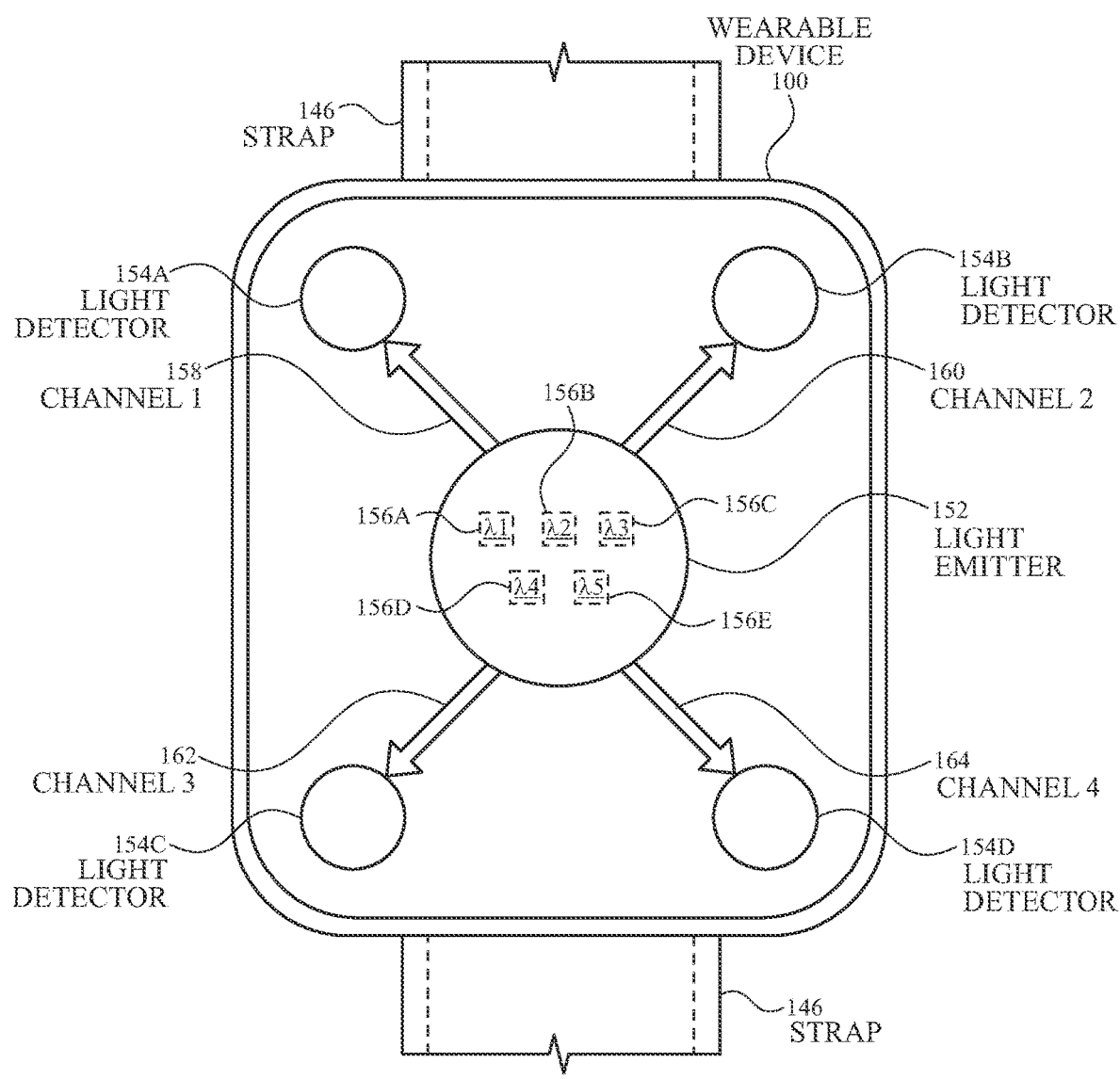
FIGS. 1D-1E illustrate alternative arrangements of light emitters and light detectors on the underside of an exemplary electronic device according to examples of the disclosure.
Figure 1E:
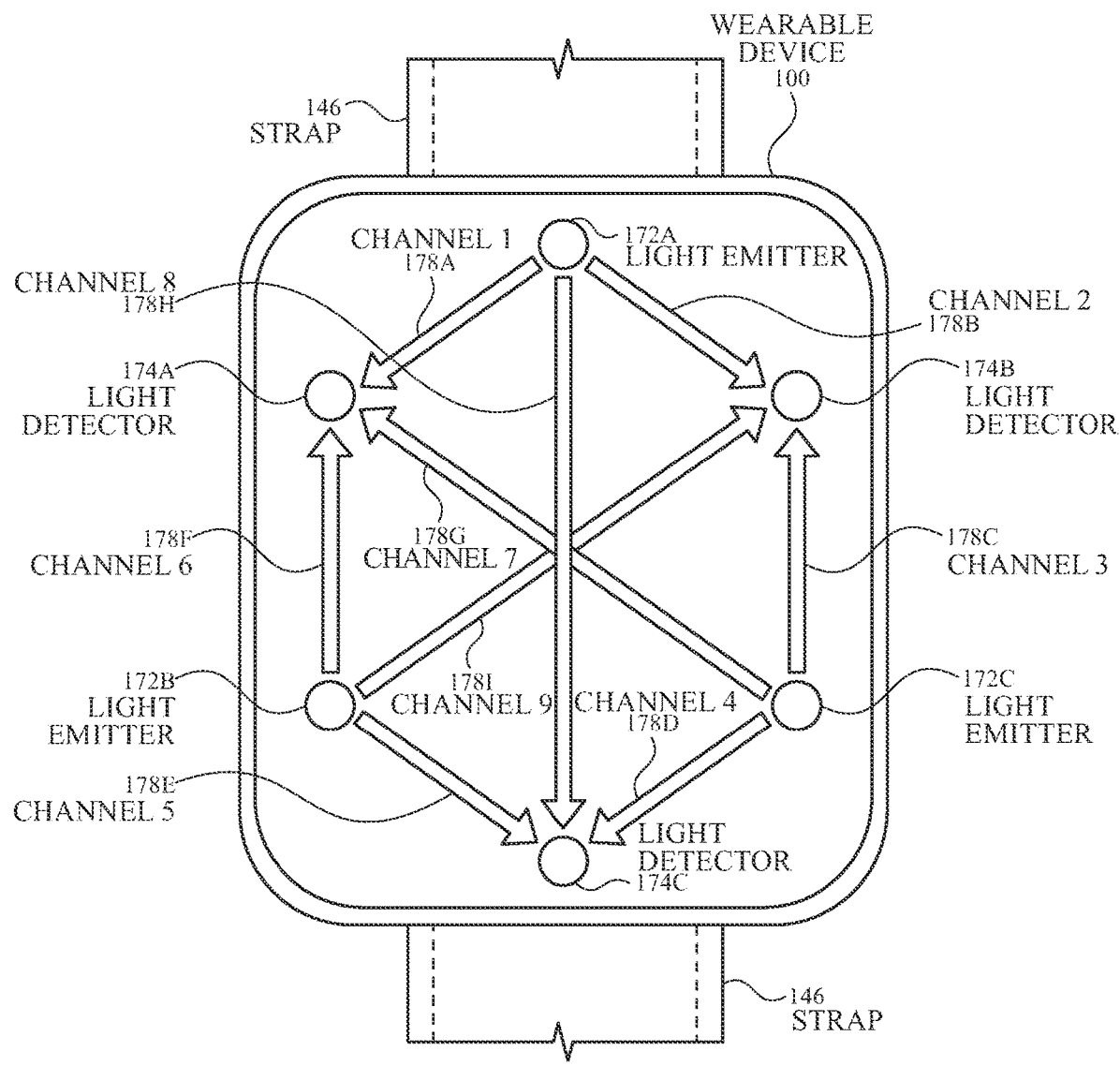

FIGS. 1D-1E illustrate alternative arrangements of light emitters and light detectors on the underside of an exemplary electronic device according to examples of the disclosure. FIG. 1D illustrates device 100 that can include light emitter 152 in a center of the device and light detectors 154A-154D. Light emitter 152 can include one or more light emitting components to generate light at different wavelengths. For example, FIG. 1D illustrates light emitter 152 including five light emitting components 156A-E (e.g., LEDs or OLEDs) configured to generate light at wavelengths $\lambda 1$, $\lambda 2$, $\lambda 3$, $\lambda 4$ and $\lambda 5$, respectively. Although five wavelengths are shown, in some examples, device 100 may include light emitting components at fewer or more wavelengths (or one tunable/filterable light emitting component) or may include different types of light emitting components (e.g., laser diodes). Light emitter 152 can be optically coupled to one or more (or each of) light detectors 154A-154D for one or more (or each of the) wavelengths. In some examples, light emitter 152 can be configured to emit light (at one or more wavelengths) detected by light detector 154A, detected by light detector 154B, detected by light detector 154C and detected by light detector 154D. As illustrated in FIG. 1D, a first channel 158 can be used to measure signal at light detector 154A from light emitter 152 (e.g., at each respective wavelength), a second channel 160 can be used to measure signal at light detector 154B from light emitter 152 (at each respective wavelength), a third channel 162 can be used to measure signal at light detector 154C from light emitter 152 (at each respective wavelength), and a fourth channel 164 can be used to measure signal at light detector 154D from light emitter 152 (at each respective wavelength). The measured signal at each detector (at each respective wavelength) can include light that has traversed various light paths (e.g., expected distributions of possible light paths through the skin and/or air) between the respective emitter and detector of the channel.

Although FIGS. 1B and 1D illustrate four channels (each operable for emitting/detecting light at multiple wavelengths), in some examples, fewer or additional channels may be implemented. For example, a single channel including one light emitter and one light detector can be used. In some examples, additional light emitters and/or light detectors may be used to form additional channels. For example, adding one or more additional light detectors to the configurations in FIG. 1B or 1D can increase the number of channels.

FIG. 1E illustrates device 100 that can include multiple light emitters 172A-172C and multiple light detectors 174A-174C arranged in a pattern around the perimeter of the device. Although the three emitters and detectors are shown in a hexagonal arrangement with an alternating pattern of emitters/detectors, it is understood that other arrangements are possible with different shaped arrangements (e.g., circle, polygon, etc.), non-alternating arrangements, and/or using more or fewer light emitters and light detectors. Light emitter 172A-172C can include one or more light emitting components (not shown) to generate light at different wavelengths (e.g., $\lambda 1$, $\lambda 2$, $\lambda 3$, etc.). Light emitters 172A-172C can be optically coupled to one or more (or each of) light detectors 174A-174C for one or more (or each of the) wavelengths. In some examples, light emitter 172A can be configured to emit light (at one or more wavelengths) detected by light detector 174A, detected by light detector 174B, and detected by light detector 174C. As illustrated in FIG. 1E, a first channel 178A can be used to measure signal at light detector 174A from light emitter 172A (e.g., at each respective wavelength), a second channel 178B can be used to measure signal at light detector 174B from light emitter 172A (at each respective wavelength), and a third channel 178H can be used to measure signal at light detector 174C from light emitter 172A (at each respective wavelength). In a similar manner, a fourth channel 178F can be used to measure signal at light detector 174A from light emitter 172B (e.g., at each respective wavelength), a fifth channel 178I can be used to measure signal at light detector 174B from light emitter 172B (at each respective wavelength), a sixth channel 178E can be used to measure signal at light detector 174C from light emitter 172B (at each respective wavelength), a seventh channel 178G can be used to measure signal at light detector 174A from light emitter 172C (e.g., at each respective wavelength), an eighth channel 178C can be used to measure signal at light detector 174B from light emitter 172C (at each respective wavelength), and a ninth channel 178D can be used to measure signal at light detector 174C from light emitter 172C (at each respective wavelength). The measured signal at each detector (at each respective wavelength) can include light that has traversed various light paths (e.g., expected distributions of possible light paths through the skin and/or air) between the respective emitter and detector of the channel.

It is understood that the light detectors of device 100 (e.g., light detector(s) 104, 104A-104B, 154A-154D, and 174A-174C) can, in some examples, include a single light detection component (e.g., photodiode or other suitable photodetector). In some examples, some or all of the light detectors of device 100 can include multiple light detection components (e.g., an array of photodiodes). Using multiple light detection components per light detector can allow for greater granularity in signal processing. Additionally or alternatively, the multiple light components can be used with different optical filters to provide simultaneous measurements for multiple wavelengths (e.g., each light detection component can include a different filter to enable measurement of a different wavelength of light).

Figure 2:
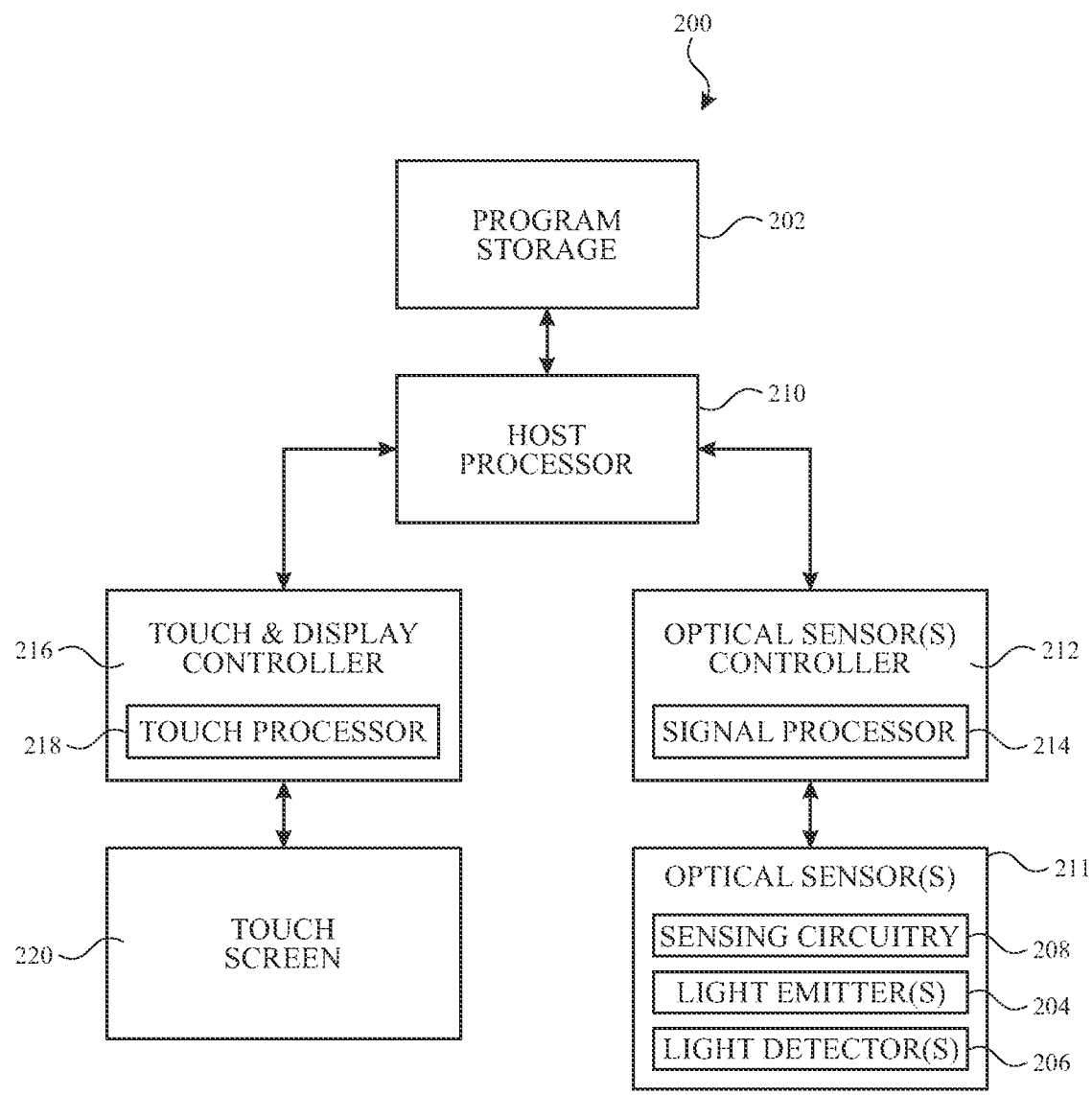
FIG. 2 illustrates an exemplary block diagram of a computing system including an optical sensor according to examples of the disclosure.

FIG. 2 illustrates an exemplary block diagram of a computing system including an optical sensor according to examples of the disclosure. Although primarily described herein as a wearable device, the computing system may alternatively be implemented partially or fully in a non-wearable device. For example, the sensors and/or processing described herein can be implemented partially or fully in a mobile telephone, media player, tablet computer, personal computer, server, etc. In some examples, the light emitters and light detectors can be implemented in a wearable device (e.g., a wristwatch) and the processing of the data can be performed in a non-wearable device (e.g., a mobile phone). Processing and/or storage of the physiological signals in a separate device can enable the device including the physiological sensors (e.g., a wristwatch) to be space and power efficient (which can be important features for portable/wearable devices).

Computing system 200 can correspond to device 100 illustrated in FIGS. 1A-1E (or may be implemented in other wearable or non-wearable electronic devices). Computing system 200 can include a processor 210 (or more than one processor) programmed to (configured to) execute instructions and to carry out operations associated with computing system 200. For example, using instructions retrieved from program storage 202, processor 210 can control the reception and manipulation of input and output data between components of computing system 200. Processor 210 can be a single-chip processor (e.g., an application specific integrated circuit) or can be implemented with multiple components/circuits.

In some examples, processor 210 together with an operating system can operate to execute computer code, and produce and/or use data. The computer code and data can reside within a program storage 202 that can be operatively coupled to processor 210. Program storage 202 can generally provide a place to hold data that is being used by computing system 200. Program storage block 202 can be any non-transitory computer-readable storage medium, and can store, for example, history and/or pattern data relating to PPG signals and relative modulation ratio (e.g., perfusion index ratio) values measured by a configuration of light emitter(s) 204 and light detector(s) 206 (e.g., as illustrated in FIG. 1B, 1D or 1E). By way of example, program storage 202 can include Read-Only Memory (ROM), Random-Access Memory (RAM), hard disk drive and/or the like. The computer code and data could also reside on a removable storage medium and loaded or installed onto computing system 200 when needed. Removable storage mediums include, for example, CD-ROM, DVD-ROM, Universal Serial Bus (USB), Secure Digital (SD), Compact Flash (CF), Memory Stick, Multi-Media Card (MMC) and/or a network component.

Computing system 200 can also include one or more input/output (I/O) controllers that can be operatively coupled to processor 210. I/O controllers can be configured to control interactions with one or more I/O devices (e.g., touch sensor panels, display screens, touch screens, physical buttons, dials, slider switches, joysticks, or keyboards). I/O controllers can operate by exchanging data between processor 210 and the I/O devices that desire to communicate with processor 210. The I/O devices and I/O controller can communicate through a data link. The data link can be a unidirectional or bidirectional link. In some cases, I/O devices can be connected to I/O controllers through wireless connections. A data link can, for example, correspond any wired or wireless connection including, but not limited to, PS/2, Universal Serial Bus (USB), Firewire, Thunderbolt, Wireless Direct, IR, RF, Wi-Fi, Bluetooth or the like.

For example, computing system 200 can include an optical sensor controller 212 operatively coupled to processor 210 and to one or more optical sensors 211. The optical sensor(s) can include light emitter(s) 204, light detector(s) 206 and corresponding sensing circuitry 208 (e.g., analog circuitry to drive emitters and measure signals at the detector, provide processing (e.g., amplification, filtering), and convert analog signals to digital signals). As described herein, light emitters 204 and light detectors 206 can be configured to generate and emit light into a user's skin and detect returning light (e.g., reflected and/or scattered) to measure a physiological signal (e.g., a PPG signal). The absorption and/or return of light at different wavelengths can also be used to determine a characteristic of the user (e.g., oxygen saturation, heart rate) and/or about the contact condition between the light emitters 204/light detectors 206 and the user's skin. Measured raw data from the light emitters 204, light detectors 206 and sensing circuitry 208 can be transferred to processor 210, and processor 210 can perform the signal processing described herein to estimate a characteristic (e.g., oxygen saturation, heart rate, etc.) of the user from the physiological signals. Processor 210 and/or optical sensor controller 212 can operate light emitters 204, light detectors 206 and/or sensing circuitry 208 to measure data from the optical sensor. In some examples, optical sensor controller 212 can include timing generation for light emitters 204, light detectors 206 and/or sensing circuitry 208 to sample, filter and/or convert (from analog to digital) signals measured from light at different wavelengths. Optical sensor controller 212 can process the data in signal processor 214 and report outputs (e.g., PPG signal, relative modulation ratio, perfusion index, heart rate, on-wrist/off-wrist state, etc.) to the processor 210. Signal processor 214 can be a digital signal processing circuit such as a digital signal processor (DSP). The analog data measured by the optical sensor(s) 211 can be converted into digital data by an analog to digital converter (ADC), and the digital data from the physiological signals can be stored for processing in a buffer (e.g., a FIFO) or other volatile or non-volatile memory (not shown) in optical sensor controller 212. In some examples, some light emitters and/or light detectors can be activated, while other light emitters and/or light detectors can be deactivated to conserve power, for example, or for time-multiplexing (e.g., to avoid interference between channels). In some examples, processor 210 and/or optical sensor controller 212 can store the raw data and/or processed information in memory (e.g., ROM or RAM) for historical tracking or for future diagnostic purposes. Additional detail regarding optical sensors and processing optical signals is described below.

Computing system 200 can also include, in some examples, a touch and display controller 216 operatively coupled to processor 210 and to touch screen 220. Touch screen 220 can be configured to display visual output in a graphical user interface (GUI), for example. The visual output can include text, graphics, video, and any combination thereof. In some examples, the visual output can include a text or graphical representation of the physiological signal (e.g., a PPG waveform) or a characteristic of the physiological signal (e.g., oxygen saturation, heart rate, etc.) Touch screen can be any type of display including a liquid crystal display (LCD), a light emitting polymer display (LPD), an electroluminescent display (ELD), a field emission display (FED), a light emitting diode (LED) display, an organic light emitting diode (OLED) display, or the like. Processor 210 can send raw display data to touch and display controller 216, and touch and display controller 216 can send signals to touch screen 220. Data can include voltage levels for a plurality of display pixels in touch screen 220 to project an image. In some examples, processor 210 can be configured to process the raw data and send the signals to touch screen 220 directly. Touch and display controller 216 can also detect and track touches or near touches (and any movement or release of the touch) on touch screen 220. For example, touch processor 218 can process data representative of touch or near touches on touch screen 220 (e.g., location and magnitude) and identify touch or proximity gestures (e.g., tap, double tap, swipe, pinch, reverse-pinch, etc.). Processor 210 can convert the detected touch input/gestures into interaction with graphical objects, such as one or more user-interface objects, displayed on touch screen 220 or perform other functions (e.g., to initiate a wake of the device or power on one or more components).

In some examples, touch and display controller 216 can be configured to send raw touch data to processor 210, and processor 210 can process the raw touch data. In some examples, touch and display controller 216 can process raw touch data itself (e.g., in touch processor 218). The processed touch data (touch input) can be transferred from touch processor 218 to processor 210 to perform the function corresponding to the touch input. In some examples, a separate touch sensor panel and display screen can be used, rather than a touch screen, with corresponding touch controller and display controller.

In some examples, the touch sensing of touch screen 220 can be provided by capacitive touch sensing circuitry (e.g., based on mutual capacitance and/or self-capacitance). For example, touch screen 220 can include touch electrodes arranged as a matrix of small, individual plates of conductive material or as drive lines and sense lines, or in another pattern. The electrodes can be formed from a transparent conductive medium such as ITO or ATO, although other partially or fully transparent and non-transparent materials (e.g., copper) can also be used. In some examples, the electrodes can be formed from other materials including conductive polymers, metal mesh, graphene, nanowires (e.g., silver nanowires) or nanotubes (e.g., carbon nanotubes). The electrodes can be configurable for mutual capacitance or self-capacitance sensing or a combination of mutual and self-capacitance sensing. For example, in one mode of operation, electrodes can be configured to sense mutual capacitance between electrodes; in a different mode of operation, electrodes can be configured to sense self-capacitance of electrodes. During self-capacitance operation, a touch electrode can be stimulated with an AC waveform, and the self-capacitance to ground of the touch electrode can be measured. As an object approaches the touch electrode, the self-capacitance to ground of the touch electrode can change (e.g., increase). This change in the self-capacitance of the touch electrode can be detected and measured by the touch sensing system to determine the positions of one or more objects when they touch, or come in proximity to without touching, the touch screen. During mutual capacitance operation, a first touch electrode can be stimulated with an AC waveform, and the mutual capacitance between the first touch electrode and a second touch electrode can be measured. As an object approaches the overlapping or adjacent region of the first and second touch electrodes, the mutual capacitance therebetween can change (e.g., decrease). This change in the mutual capacitance can be detected and measured by the touch sensing system to determine the positions of one or more objects when they touch, or come in proximity to without touching, the touch screen. In some examples, some of the electrodes can be configured to sense mutual capacitance therebetween and some of the electrodes can be configured to sense self-capacitance thereof.

Note that one or more of the functions described herein, including estimating a physiological characteristic according to examples of the disclosure, can be performed by firmware stored in memory (or in program storage 202) and executed by physiological sensor controller 212, touch and display controller 216 or processor 210. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Referring back to FIG. 1B, light emitters 102A-102B can generate light and light detectors 104A-104B can measure light at multiple wavelengths (e.g., $\lambda 1$, $\lambda 2$, $\lambda 3$). In some examples, three light emitting components 106A-106C can be co-located (within a threshold distance of one another, e.g., less than 5 mm) in each of light emitters 102A-102B. In some examples, each of the light emitting components can be driven in a time-multiplexed manner. For example, during a measurement period of duration T (from time t0 to t6), a first light emitting component 106A of light emitter 102A can be driven at wavelength $\lambda 1$ and light can be detected at light detectors 104A-104B (from t0 to t1), a second light emitting component 106B of light emitter 102A can be driven at wavelength $\lambda 2$ and light can be detected at light detectors 104A-104B (from t1 to t2), a third light emitting component 106C of light emitter 102A can be driven at wavelength $\lambda 3$ and light can be detected at light detectors 104A-104B (from t2 to t3), a fourth light emitting component 106A of light emitter 102B can be driven at wavelength $\lambda 1$ and light can be detected at light detectors 104A-104B (from t3 to t4), a fifth light emitting component 106B of light emitter 102B can be driven at wavelength $\lambda 2$ and light can be detected at light detectors 104A-104B (from t4 to t5), and a sixth light emitting component 106C of light emitter 102B can be driven at wavelength $\lambda 3$ and light can be detected at light detectors 104A-104B (from t5 to t6). Ideally, the measurement period can be less than a threshold duration. Reducing the duration of measurement period can allow for the measurements at different wavelengths to be as co-located in time as possible. In some examples, the duration of the measurement period can be less than 100 ms. The above measurements can result in a sample for each channel (e.g., four channels of FIG. 1B, 9 channels for FIG. 1E) at each wavelength (e.g., $\lambda 2$, $\lambda 3$) for the measurement period. The sample for each channel can be used to compute physiological characteristics such as perfusion indices, perfusion index ratios, SpO2, etc. In some examples, the light emitting components can be frequency-multiplexed such that multiple light emitting components to concurrently emit light and detectors can differentiate between the light emitting components based on the frequency content.

Figure 3A:
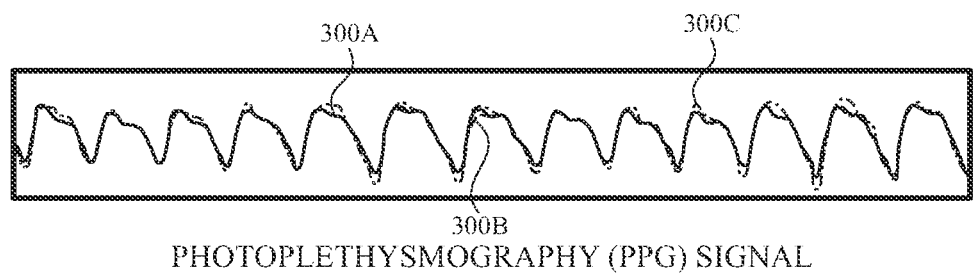
FIGS. 3A-3B illustrate example photoplethysmogram (PPG) signals measured at different wavelengths according to examples of the disclosure.
Figure 3B:
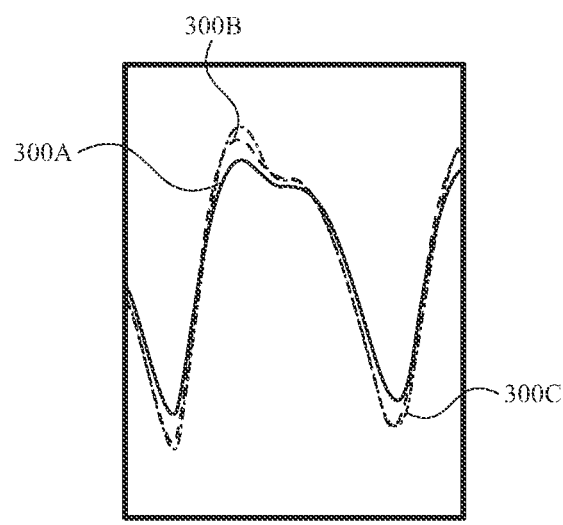

FIGS. 3A-3B illustrate example photoplethysmogram (PPG) signals measured at different wavelengths according to examples of the disclosure. The PPG signals can include cyclical "beats" (or "pulses") corresponding to a heartbeat (e.g., each "beat" or "pulse" indicative of one occurrence of the repeating cardiac cycle). FIGS. 3A-3B illustrate a PPG signal for each of wavelengths 1, $\lambda 2$ and $\lambda 3$ (e.g., while device 100 is properly secured to skin 120 to establish good contact between the optical sensor(s) and the skin). FIG. 3A illustrates PPG signals 300A, 300B, 300C with multiple beats and FIG. 3B illustrates a larger view of an exemplary beat, in which the waveform shapes of PPG signals 300A-300C can be similar and correspond to pulsatile blood information. Although not shown in FIGS. 3A-3B, in some examples, when device is not properly secured to skin 120 (light or poor content), the waveform of PPG signal can be different in shape and/or relative amplitude (and may or may not correspond to pulsatile blood information) for wavelength $\lambda 3$ (e.g., different than the shape and/or relative amplitude of PPG signal 300C, whereas the waveforms of PPG signals 300A and 300B may be similar even with poorer contact between the optical sensor and tissue). As a result, poor contact conditions may result in an inaccurate estimate of the physiological signal characteristic.

In some examples, a sensor can be used to estimate a contact condition. For example, device 100 can include a touch sensor (e.g., capacitive, resistive, ultrasonic, etc.), proximity sensor (e.g., an infrared sensor), force sensor or other suitable sensor separate from optical sensor(s) 211 on the underside of the device to estimate a contact condition between device 100 can the user's tissue. In some examples, one or more channels of optical sensor 211 can be used to estimate the contact condition. In some examples, measurements at wavelength $\lambda 3$ (e.g., green light, blue light, etc.) can be used to estimate the contact condition (or more generally contribute to quality metrics) and identify which channels include measurements at wavelengths $\lambda 1$ and $\lambda 2$ (e.g., red light and IR light) that may be suitable for physiological signal processing and/or how to process the measurements at wavelengths $\lambda 1$ and $\lambda 2$ in the physiological signal processing. In some examples, when poor contact conditions are estimated based on wavelengths $\lambda 3$ (e.g., when the device is outside a threshold distance from the surface of the user's skin or in poor contact) or based on another sensor (e.g., touch, proximity, force, etc.), the device can forgo estimating or reporting an estimated physiological characteristic based on wavelengths λ1 and λ2 (e.g., per channel or for all channels of the device). Although beats are shown, it is understood that the methods described herein can be applied based on instantaneous measurements, on a beat-by-beat basis, on an average of multiple beats, or after converting to a different domain, such as a frequency domain (e.g., using a Fourier transform) or wavelet domain.

Other conditions aside from contact condition may result in an inaccurate estimate of the physiological signal characteristic. For example, while device 100 is at an unexpected orientation relative to skin 120 or in the presence of transient or permanent tissue variations, measurements at wavelengths λ1 and λ2 (PPG signals) may result in inaccurate measurements of the physiological signal characteristic, despite the PPG signals having quality characteristics consistent with physiologically valid PPG signals showing a consistent cardiac signal indicative of accurate measurements of the physiological signal characteristic. In some examples, when these conditions are detected, the device can forgo estimating or reporting an estimated physiological characteristic (e.g., under the assumption that the measurement may be inaccurate).

As described herein, an optical sensor with one or more light emitters (e.g., each including a red LED and an IR LED) and light detectors (e.g., a photodetector) can be used for pulse oximetry. When placed in contact with a blood-perfused tissue bed such as the skin, the detected photo signals from the light emitter may be fractionally modulated (AC/DC) by the pulsing arterial blood content in the tissues (e.g., as a result of beat-to-beat pumping of blood by the heart over the cardiac cycle). The ratio of the red and IR modulation in these detected pulsatile signals (modulation ratio "R") can correlate to the oxygenation state (saturation) of the hemoglobin in arterial blood (SaO2) because oxygenated and deoxygenated hemoglobin absorb red and IR light to a different extent. The correlation between modulation ratio R and SaO2 can be empirically measured and can be used to define a calibration curve or calibration relationship for the optical sensors. For example, an optical sensor can be calibrated empirically by mapping modulation ratio R measured using the optical sensor of the pulse oximeter system to the SaO2 (e.g., measured using another calibrated device, or from simultaneous arterial blood draws analyzed via co-oximetry) across a targeted saturation span (e.g., 70-100% SaO2) on one or more users (e.g., a group of healthy volunteers). During operation of the optical sensor, the calibration relationship can be used to estimate SaO2 by pulse oximetry (e.g., using measurements of modulation ratio by the optical sensor and the calibration relationship to estimate SpO2).

As described herein, in some examples, the optical sensor can include multiple channels. In some examples, the multiple channels can be of a uniform distance (e.g., the distance between the emitter and detector for each channel can be the same across channels). In some examples, the multiple channels can have different distances such that the optical sensor includes distance asymmetries among the channels. Distances between emitters and detectors as used herein can be defined by the centers of their respective apertures, by their respective nearest edges, or by an alternative metric such as a midpoint between the center and edge of the aperture. In some examples, even when multiple channels can be of a uniform distance, the placement of the light emitting components (e.g., red LED, IR LED die placement) within the emitter can result in overall effective distance asymmetries among the channels. Physical separation and/or differing radiation patterns between the light emitting components within an emitter may result in different respective light energy distributions and/or emission angles at the skin surface. In some examples, the multiple channels can emit light at uniform wavelengths (e.g., each emitter can include a red LED emitting light at a first wavelength an IR LED emitting light at a second wavelength). In some examples, the multiple channels can emit light at different wavelengths (e.g., emitters can include red LEDs emitting light at different wavelengths within a spectrum of red light and emitters can include IR LEDs emitting light at different wavelengths within a spectrum of IR light). In some examples, to improve the reliability of the SpO2 estimate, the optical sensor can use multiple different calibration relationships (e.g., calibration curves) for the multiple channels to account for differences in the calibration relationship between modulation ratio R-to-SaO2 due to the asymmetric wavelength characteristics (e.g., different red and/or IR LED wavelengths) and asymmetric distance characteristics (e.g., different distances between the emitter and detector and/or effective distances caused by the light emitting components within the emitters).

Figure 4A:
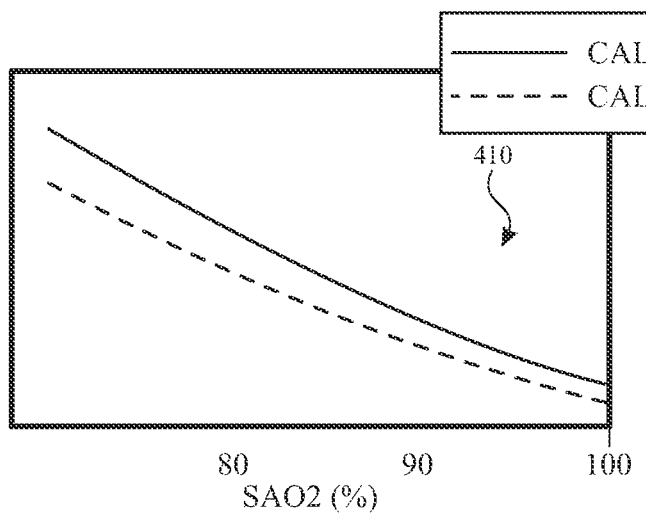
FIGS. 4A-4C illustrate example light emitting component placement and corresponding calibration relationships according to examples of the disclosure.
Figure 4A:
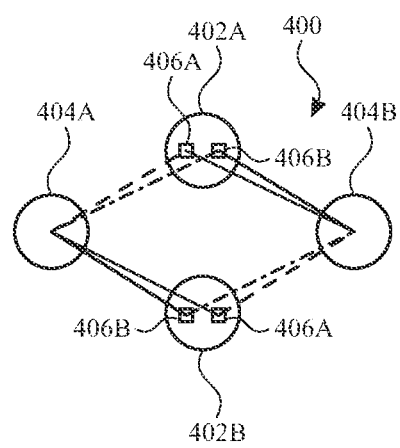
Figure 4B:
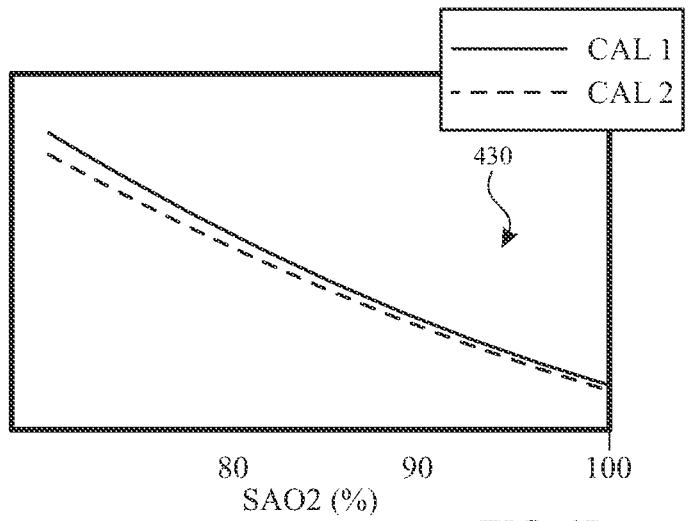
Figure 4B:
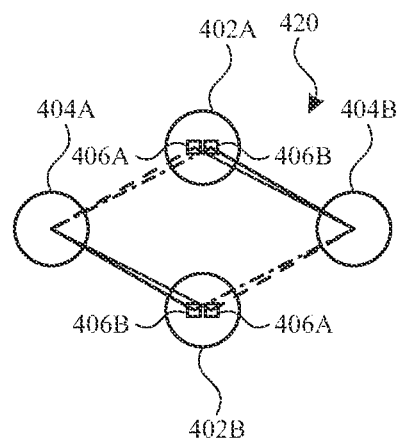
Figure 4C:
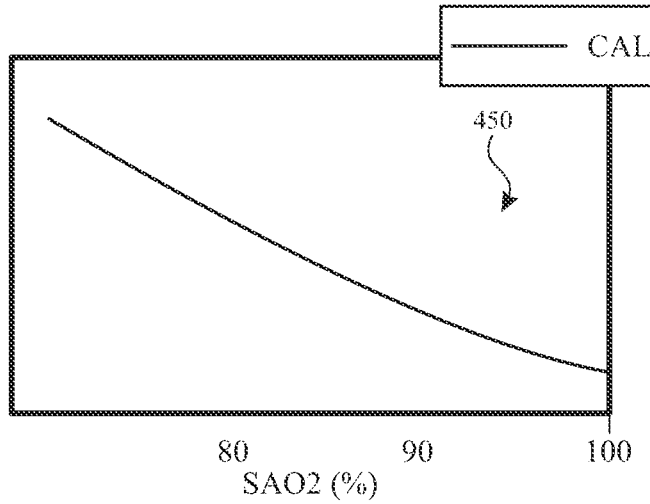
Figure 4C:
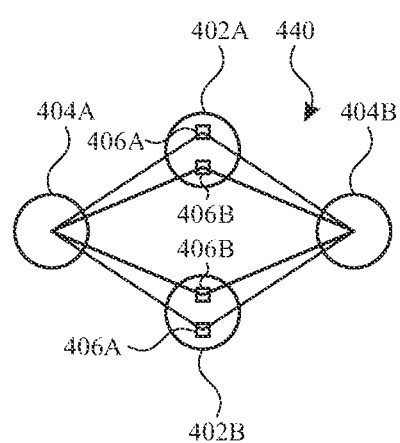

FIGS. 4A-4C illustrate example light emitting component placement and corresponding calibration relationships according to examples of the disclosure. FIGS. 4A-4C illustrate configurations 400, 420, and 440 of four equidistant channels between light emitters 402A-402B and light detectors 404A-404B, similar to the configuration of emitters/detectors in FIG. 1B. Configurations 400, 420, and 440 include different die placements of light emitting components (e.g., LEDs, OLEDs, etc.) within emitters 402A-402B that may impact the overall channel distance between the light emitting components within the emitter and the detector. In configurations 400 and 420 the light emitting components within the emitters are horizontally spaced such that the distance between the red LEDs 406A and the IR LEDs 406B to the detectors 404A-404B are different for different channels. For example, dashed line channels can have a ratio of distance between red LED and detector ($D_{red}$) to distance between IR LED and detector ($D_{IR}$) of less than one (e.g., $D_{red}/D_{IR}<1$), whereas solid line channels can have a ratio of distance between red LED and detector ($D_{red}$) to distance between IR LED and detector ($D_{IR}$) of greater than one (e.g., $D_{red}/D_{IR}>1$). As a result of the different distances, two calibration relationships can be used for the four channels. Plots 410 and 430 corresponding to configurations 400 and 420, respectively, show two calibration relationships between modulation ratio R and oxygen saturation with solid-line calibration curve "CAL1" and dashed line calibration curve "CAL2." Solid-line calibration curve "CAL1" can represent the calibration curve for solid line channels in configurations 400 and 420 (e.g., between emitter 402A and detector 404B and between emitter 402B and detector 404A), and dashed-line calibration curve "CAL2" can represent the calibration curve for dashed-line channels in configurations 400 and 420 (e.g., between emitter 402A and detector 404A and between emitter 402B and detector 404B).

As shown in FIGS. 4A-4B as the separation distance between the red LEDs 406A and the IR LEDs 406B increases within the emitter, the separation between the calibration relationships increase. For example, configuration 400 with greater separation between the red LEDs 406A and the IR LEDs 406B has greater separation between calibration curves "CAL1" and "CAL2" as compared with the reduced separation between calibration curves "CAL1" and "CAL2" for configuration 420 with lesser separation between the red LEDs 406A and the IR LEDs 406B. In some examples, a different number of calibration curves can be used for the channels of configurations 400 and 420. In some examples, when the separation between the calibration curves is less than a threshold (e.g., such that SpO2 estimates are within specification), the same calibration curve can be used for all the channels of configurations 400 and 420.

The description of FIGS. 4A-4B assume that the distances for red and IR LEDs to detectors are the same for the pairs of channels (e.g., there are two values of $D_{red}/D_{IR}$ for the four channels). It is understood that in some examples, there may be four different values of $D_{red}/D_{IR}$ for the four channels and four different calibration relationships. In some such examples, four different calibration curves can be used for the four channels (e.g., unique calibration curve for each channel), or in some examples, fewer calibration curves can be used for the four channels (e.g., one calibration curve can be used for four similarly spaced channels, two calibration curves can be used for pairs of similar spaced channels, etc.).

For comparison, FIG. 4C illustrates configuration 440 with light emitting components within the emitters vertically spaced such that the distance between the red LEDs 406A and the IR LEDs 406B to the detectors 404A-404B can be uniform different channels (e.g., $D_{red}/D_{IR}$ is uniform across channels). As a result, one calibration relationship can be used for the four channels. Plot 450 corresponding to configuration 440 shows one calibration relationship between modulation ratio R and oxygen saturation with calibration curve "CAL1." A similar result could be achieved for emitters using one wavelength-tunable light source.

Although FIGS. 4A-4C primarily focus on the placement of light emitting components within the light emitters in terms of die position, it is understood that different angles of light emitting components can also impact the effective distances and therefore the expected distributions of possible light paths for different channels (even in the instance of FIG. 4C with uniform $D_{red}/D_{IR}$ across channels). For example, die placement for light emitting components with different angles for different channels can result in different effective distances for the channels that can be accounted for using one or more angle-dependent calibration curves.

In a similar manner as described with respect to FIGS. 4A-4C for symmetric distances between emitters/detectors, but with asymmetric overall effective distances due to light emitting component die placement within the emitters, different calibration relationships (e.g., calibration curves) can be used for asymmetric distances between emitters and detectors among the channels. For example, FIG. 1E illustrates an optical sensor with asymmetric distances between channels. A first set of channels can have a first distance and a second set of channels can have a second distance. For example, channels 1-6 can have a shorter distance along the perimeter of the arrangement of light emitters 172A-172C and light detectors 174A-174C compared with channels 7-9 that can have a longer distance across the center of the arrangement of light emitters 172A-172C and light detectors 174A-174C. In some such examples, a first calibration relationship can be used for the channels 1-6 and a second, different calibration relationship can be used for channels 7-9. Although two different calibration curves are described for two sets of channels, it is understood that more or fewer calibration curves can be used. For example, a unique calibration curve can be used for each channel (e.g., 9 calibration curves in the configuration of FIG. 1E, three calibration curves can be used (e.g., each for three channels), or one calibration curve can be used for all channels). The number of calibration relationships/calibration curves can be determined based on the amount of separation between the calibration curves for each channel and/or how many unique calibration curves may be required to meet an accuracy specification for the optical sensor.

In a similar manner to distance-dependent calibration relationships, wavelength dependent calibration relationships can be generated and used to account for wavelength asymmetry across different channels. In some examples, a unique wavelength-dependent calibration curve can be used for each channel. In some examples, a single calibration curve can be used for each channel (e.g., assuming no wavelength-asymmetry or less than a threshold asymmetry). In some examples, multiple calibration curves can be used for sets of channels that share similar wavelength characteristics. The number of calibration relationships (e.g., calibration curves) can be determined based on the amount of separation between the calibration curves for each channel and/or how many unique calibration curves may be required to meet an accuracy specification for the optical sensor.

Although described separately, calibration relationships for the multiple channels can be derived for the distance between emitters and detectors, die placement within the emitters and/or wavelength. In some examples, a unique calibration relationship can be used for each channel. In some examples, a single calibration relationship can be used for all channels. In some examples, multiple calibration relationships can be used for sets of channels that share similar characteristics (emitter/detector and/or die placement characteristic, wavelength characteristic). The number of calibration relationships (e.g., calibration curves) can be determined based on the amount of separation between the calibration curves for each channel and/or how many unique calibration curves may be required to meet an accuracy specification for the optical sensor.

Figure 5:
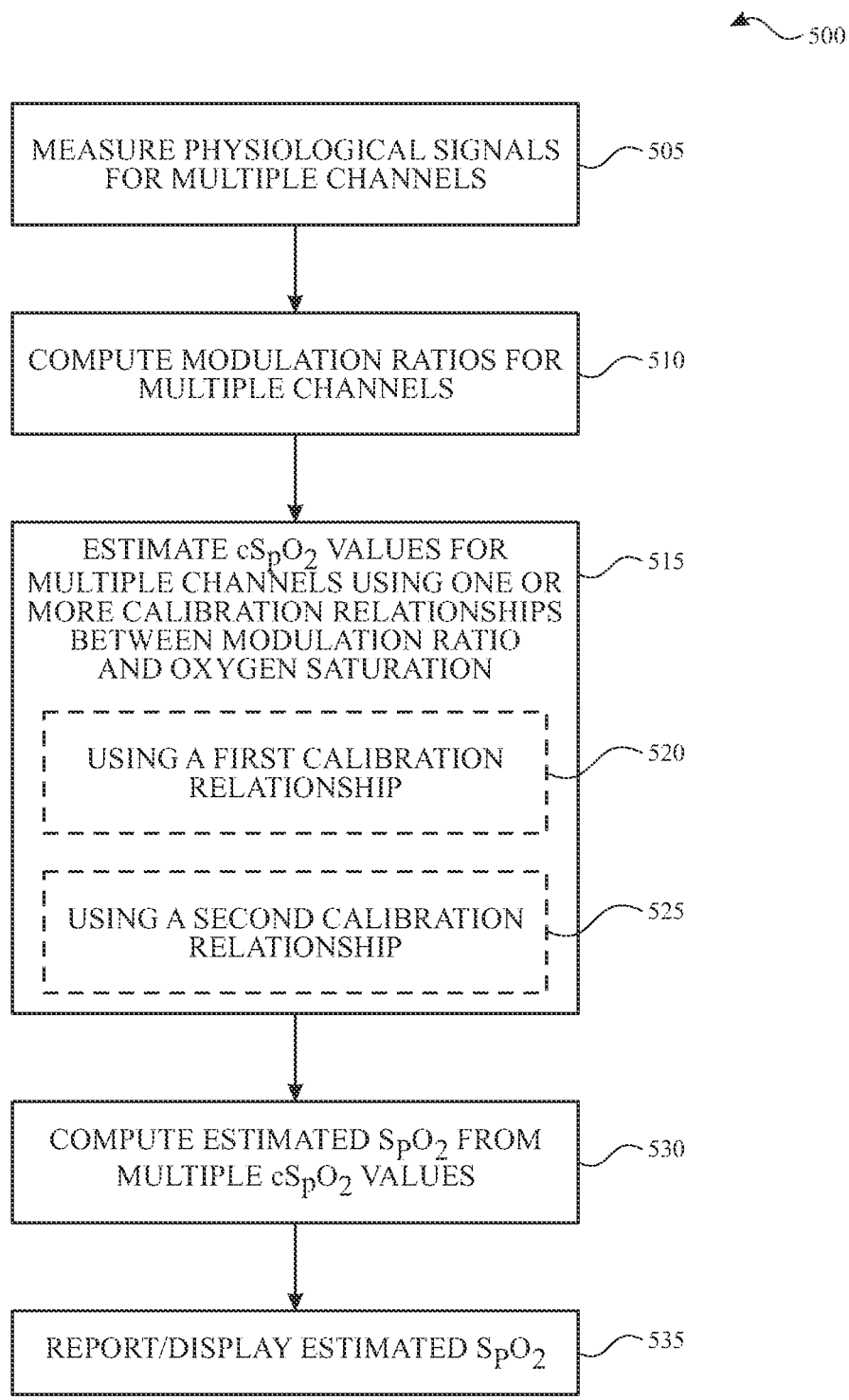
FIG. 5 illustrates an example process for asymmetric distance-dependent and/or wavelength-dependent calibration according to examples of the disclosure.

FIG. 5 illustrates an example process 500 for asymmetric distance-dependent and/or wavelength-dependent calibration according to examples of the disclosure. At 505, physiological signals can be measured for multiple channels. For example, each channel of the optical sensor(s) 211 (e.g., channels 108, 110, 112, and 114 for the configuration of FIG. 1B, channels 158, 160, 162 and 164 for the configuration of FIG. 1D, or channels 178A-178I for the configuration of FIG. 1) can measure light at two or more different wavelengths (e.g., red, IR, etc.). In some examples, one or more quality metrics can be calculated for the multiple channels. In some examples, the quality metric can be a quality score (e.g., between zero and one) with higher scores corresponding to physiologically valid PPG signals showing a consistent cardiac signal. In some examples, the channel quality score can be determined based on one or more quality metrics including: the signal-to-noise ratio (SNR) of the optical sensor hardware, the morphology of the PPG signals, the phase consistency between the PPG signals at different wavelengths (e.g., red, IR, green), correlation between the PPG signals at different wavelengths (e.g., red, IR, green), beat-to-beat consistency (correlation of heartbeats) in the PPG signal, and/or harmonic consistency in the PPG signal. In some examples, channels with quality metrics/quality scores below a threshold(s) can be discarded and not used for estimating an SpO2 value. At 510, modulation ratios can be computed for multiple channels. For example, the modulation ratio R can be computed as a perfusion index ratio between the measurements at the different wavelengths (e.g., red and IR).

At 515, physiological characteristics can be estimated for multiple channels. In some examples, a "cSpO2" value can be estimated for each channel (where the "c" indicates that the cSpO2 value is one of multiple channels values that can be used in determining a final SpO2). The cSpO2 can be estimated for each channel using the modulation ratio R (e.g., perfusion index ratio between the measurements at the different wavelengths) and using one of one or more calibration relationships between modulation ratio R and oxygen saturation. In some examples, as described herein, multiple calibration relationships can be used to account for asymmetric characteristics (e.g., distance, wavelength). For example, a first calibration relationship can be used for one or more channels (e.g., a first set of channels) (520), and a second calibration relationship can be used for one or more different channels (e.g., a second set of channels) (525). For example, as discussed above, an optical sensor with an arrangement of FIG. 1E having two different emitter/detector distances for different channels can use a first calibration relationship for channels having a first distance (e.g., channels 1-6) and second calibration relationship for channels having a second distance (e.g., channels 7-9). In some examples, a third calibration relationship can be used for a third set of channels if appropriate, etc. In some examples, a unique calibration relationship can be used for each channel of the multiple channels.

In some examples, the estimation of cSpO2 values for the multiple channels can be performed using one or more lookup tables, where the lookup table(s) implement the calibration relationships such that an input modulation ratio R can provide an output estimated cSpO2 value. In some examples, the estimation of cSpO2 values for the multiple channels can be performed using an equation representing or approximating the calibration relationship (e.g., using coefficients of a polynomial fit to the calibration curve, etc.), such that the input modulation ratio R can provide an output cSpO2 value. In some examples, the inputs can include wavelength information and/or distance information (emitter-detector distance and/or die placement information), such that the lookup table and/or equation can account for asymmetric characteristic(s).

In some examples, the number of calibration relationships can be reduced by using a correction factor to account for wavelength dependence and/or distance dependence. For example, rather than using two different calibration relationships for the two different emitter-detector distances for the configuration of FIG. 1E, a single calibration relationship can be used and a correction factor can be applied to some channels (e.g., to the estimated cSpO2, to the modulation ratio, or to the calibration relationship to scale the calibration curve) to account for the distance-dependence (e.g., different distances between emitter/detector pairs, different effective distances due to die placement, etc.). Additionally or alternatively, in a similar manner, a correction factor can be used to account for wavelength dependence. In some examples, different emitter/detector pair distances and die-placement asymmetry may be combined into sets of common calibration relationships for like channels (e.g., nominal coefficients to a mathematical relationship that are applicable to common channels), with some or all of the coefficients additionally including correction factors to account for wavelength dependence.

At 530, an estimated physiological characteristic can be computed using the multiple cSpO2 values for the multiple channels. For example, the physiological characteristic can be computed by averaging the multiple cSpO2 values (or at least those with quality metrics/scores above a threshold). In some examples, the averaging may include a weighting factor (e.g., a weighted average). In some examples, prior to being averaged, one or more of the multiple cSpO2 values may be rejected or down-weighted based on a set of heuristic rules (e.g., outlier rejection, and/or spatially-dependent discrepancies in their values). In some examples, the estimated physiological characteristic can be reported to the user at 535. For example, the estimated physiological characteristic can be displayed on the display, can be stored on the device or transmitted to another device, or can be reported with other feedback mechanisms (e.g., audio feedback, haptic feedback, etc.).

Process 500 can be performed at an electronic device such as device 100 or 200 (e.g., by processor 210 and/or by signal processor 214). It should be understood that the particular order of the description of the operations in process is merely exemplary and is not intended to indicate that the described order is the only order in which the operations could be performed. One of ordinary skill in the art would recognize various ways to reorder the operations described herein (e.g., some operations of process 500 can be combined, reordered and/or omitted). For example, process 500 can receive physiological signals and/or modulation ratios for the multiple channels and begin the process at 510 or 515. Likewise, process 500 can omit reporting/displaying the physiological characteristics at 535.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, monitoring physiological characteristics, such SpO2, may allow a user to track or otherwise gain insights about their health.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to an electronic device, such as a wearable device. The wearable device can comprise: an optical sensor including a plurality of channels and configured to measure physiological signals from the plurality of channels, and a processor (processing circuitry) coupled to the optical sensor. Each of the plurality of channels can be defined by a light emitter and a light detector. A first channel of the plurality of channels can have a first expected distribution of light paths and a second channel of the plurality of channels can have a second expected distribution of light paths different from the first expected distribution of light paths. The processor can be programmed to: calculate a first modulation ratio for the first channel and a second modulation ratio for the second channel; estimate a first cSpO2 value using the first modulation ratio and a first calibration relationship between modulation ratio and oxygen saturation; estimate a second cSpO2 value using the second modulation ratio and a second calibration relationship between modulation ratio and oxygen saturation, different from the first calibration relationship; and compute an SpO2 estimate using the first cSpO2 value and the second cSpO2 value. Additionally or alternatively to one or more of the examples disclosed above, in some examples, the first channel can have the first expected distribution of light paths due to a first separation distance between a first light emitter and a first light detector of the first channel; and the second channel can have the second expected distribution of light paths due to a second separation distance between a second light emitter and a second light detector of the second channel, different from the first separation distance. Additionally or alternatively to one or more of the examples disclosed above, in some examples, the first channel can have the first expected distribution of light paths due to a first separation distance between a light emitting component within a first light emitter and a first light detector of the first channel or due to a first angle of the first light emitting component within the first light emitter; the second channel can have the second expected distribution of light paths due to a second separation distance between a light emitting component within a second light emitter and a second light detector of the second channel or due to a second angle of the light emitting component within a second light emitter; and the first separation distance can be different from the second separation distance or the first angle is different from the second angle. Additionally or alternatively to one or more of the examples disclosed above, in some examples, the first channel can have the first expected distribution of light paths due to a first wavelength of a light emitting component of a first light emitter of the first channel; and the second channel can have the second expected distribution of light paths due to a second wavelength of a light emitting component of a second light emitter of the second channel different from the first wavelength. Additionally or alternatively to one or more of the examples disclosed above, in some examples, a third channel of the plurality of channels can have the first expected distribution of light paths and a fourth channel of the plurality of channels can have the second expected distribution of light paths. The processor can be further programmed to: calculate a third modulation ratio for the third channel and a fourth modulation ratio for the fourth channel; estimate a third cSpO2 value using the third modulation ratio and the first calibration relationship between modulation ratio and oxygen saturation; estimate a fourth cSpO2 value using the fourth modulation ratio and the second calibration relationship between modulation ratio and oxygen saturation; and compute the SpO2 estimate using the first cSpO2 value, the second cSpO2 value, the third cSpO2 value, and the fourth cSpO2 value. Additionally or alternatively to one or more of the examples disclosed above, in some examples, the first channel and the third channel can have the first expected distribution of light paths due to a first separation distance between a first light emitter and a first light detector of the first channel and the first separation distance between a third light emitter and a third light detector of the third channel; and the second channel and the fourth channel can have the second expected distribution of light paths due to a second separation distance, different from the first separation distance, between a second light emitter and a second light detector of the second channel and the second separation distance between a fourth light emitter and a fourth light detector of the fourth channel. Additionally or alternatively to one or more of the examples disclosed above, in some examples, a third channel of the plurality of channels can have the first expected distribution of light paths. The processor can be further programmed to: calculate a third modulation ratio for the third channel; estimate a third cSpO2 value using the third modulation ratio and the first calibration relationship between modulation ratio and oxygen saturation; and compute the SpO2 estimate using the first cSpO2 value, the second cSpO2 value, and the third cSpO2 value. Additionally or alternatively to one or more of the examples disclosed above, in some examples, a third channel of the plurality of channels can have the first expected distribution of light paths and a fourth channel of the plurality of channels can have the second expected distribution of light paths. The processor can be further programmed to: calculate a third modulation ratio for the third channel and a fourth modulation ratio for the fourth channel; estimate a third cSpO2 value using the third modulation ratio and a third calibration relationship between modulation ratio and oxygen saturation, different from the first calibration relationship and the second calibration relationship; estimate a fourth cSpO2 value using the fourth modulation ratio and a fourth calibration relationship between modulation ratio and oxygen saturation, different from the first calibration relationship, the second calibration relationship, and the third calibration relationship; and compute the SpO2 estimate using the first cSpO2 value, the second cSpO2 value, the third cSpO2 value, and the fourth cSpO2 value. Additionally or alternatively to one or more of the examples disclosed above, in some examples, the second calibration relationship between modulation ratio and oxygen saturation can be generated by applying a distance-dependent correction factor to the first calibration relationship between modulation ratio and oxygen saturation. Additionally or alternatively to one or more of the examples disclosed above, in some examples, the first calibration relationship or the second calibration relationship can include a wavelength-dependent correction factor.

Some examples of the disclosure are directed to a method. The method can comprise: calculating a first modulation ratio for a first channel of an optical sensor having a first expected distribution of light paths and a second modulation ratio for the second channel of the optical sensor having a second expected distribution of light paths different from the first expected distribution of light paths; estimating a first cSpO2 value using the first modulation ratio and a first calibration relationship between modulation ratio and oxygen saturation; estimating a second cSpO2 value using the second modulation ratio and a second calibration relationship between modulation ratio and oxygen saturation, different from the first calibration relationship; and computing an SpO2 estimate using the first cSpO2 value and the second cSpO2 value. Additionally or alternatively to one or more of the examples disclosed above, in some examples, the first channel can have the first expected distribution of light paths due to a first separation distance between a first light emitter and a first light detector of the first channel; and the second channel can have the second expected distribution of light paths due to a second separation distance between a second light emitter and a second light detector of the second channel, different from the first separation distance. Additionally or alternatively to one or more of the examples disclosed above, in some examples, the first channel can have the first expected distribution of light paths due to a first separation distance between a light emitting component within a first light emitter and a first light detector of the first channel or due to a first angle of the first light emitting component within the first light emitter; the second channel can have the second expected distribution of light paths due to a second separation distance between a light emitting component within a second light emitter and a second light detector of the second channel or due to a second angle of the light emitting component within a second light emitter; and the first separation distance can be different from the second separation distance or the first angle is different from the second angle. Additionally or alternatively to one or more of the examples disclosed above, in some examples, the first channel can have the first expected distribution of light paths due to a first wavelength of a light emitting component of a first light emitter of the first channel; and the second channel can have the second expected distribution of light paths due to a second wavelength of a light emitting component of a second light emitter of the second channel different from the first wavelength. Additionally or alternatively to one or more of the examples disclosed above, in some examples, a third channel of the optical sensor can have the first expected distribution of light paths and a fourth channel of the plurality of channels can have the second expected distribution of light paths. The method can further comprise: calculating a third modulation ratio for the third channel and a fourth modulation ratio for the fourth channel; estimating a third cSpO2 value using the third modulation ratio and the first calibration relationship between modulation ratio and oxygen saturation; estimating a fourth cSpO2 value using the fourth modulation ratio and the second calibration relationship between modulation ratio and oxygen saturation; and computing the SpO2 estimate using the first cSpO2 value, the second cSpO2 value, the third cSpO2 value, and the fourth cSpO2 value. Additionally or alternatively to one or more of the examples disclosed above, in some examples, the first channel and the third channel can have the first expected distribution of light paths due to a first separation distance between a first light emitter and a first light detector of the first channel and the first separation distance between a third light emitter and a third light detector of the third channel; and the second channel and the fourth channel can have the second expected distribution of light paths due to a second separation distance, different from the first separation distance, between a second light emitter and a second light detector of the second channel and the second separation distance between a fourth light emitter and a fourth light detector of the fourth channel. Additionally or alternatively to one or more of the examples disclosed above, in some examples, a third channel of the optical sensor can have the first expected distribution of light paths. The method can further comprise: calculating a third modulation ratio for the third channel; estimating a third cSpO2 value using the third modulation ratio and the first calibration relationship between modulation ratio and oxygen saturation; and computing the SpO2 estimate using the first cSpO2 value, the second cSpO2 value, and the third cSpO2 value. Additionally or alternatively to one or more of the examples disclosed above, in some examples, a third channel of the optical sensor can have the first expected distribution of light paths and a fourth channel of the optical sensor can have the second expected distribution of light paths. The method can further comprise: calculating a third modulation ratio for the third channel and a fourth modulation ratio for the fourth channel; estimating a third cSpO2 value using the third modulation ratio and a third calibration relationship between modulation ratio and oxygen saturation, different from the first calibration relationship and the second calibration relationship; estimating a fourth cSpO2 value using the fourth modulation ratio and a fourth calibration relationship between modulation ratio and oxygen saturation, different from the first calibration relationship, the second calibration relationship, and the third calibration relationship; and computing the SpO2 estimate using the first cSpO2 value, the second cSpO2 value, the third cSpO2 value, and the fourth cSpO2 value. Additionally or alternatively to one or more of the examples disclosed above, in some examples, the second calibration relationship between modulation ratio and oxygen saturation can be generated by applying a distance-dependent correction factor to the first calibration relationship between modulation ratio and oxygen saturation. Additionally or alternatively to one or more of the examples disclosed above, in some examples, the first calibration relationship or the second calibration relationship can include a wavelength-dependent correction factor. Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Some examples of the disclosure are directed to an electronic device, such as a wearable device. The wearable device can comprise: an optical sensor including a plurality of channels including channels with asymmetric distances and configured to measure physiological signals from the plurality of channels; and a processor (processing circuitry) coupled to the optical sensor. The processor can be programmed to: compute an SpO2 estimate using a plurality of modulation ratios from the plurality of channels and using distance-dependent calibration relationships between modulation ratio and oxygen saturation.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A device comprising:
an optical sensor including a plurality of channels and configured to measure physiological signals from the plurality of channels, wherein each of the plurality of channels is defined by a light emitter and a light detector, and wherein a first channel of the plurality of channels has a first expected distribution of light paths and a second channel of the plurality of channels has a second expected distribution of light paths different from the first expected distribution of light paths; and
a processor coupled to the optical sensor and programmed to:
   determine a first modulation ratio for the first channel and a second modulation ratio for the second channel;
   estimate a first channel physiological characteristic value using the first modulation ratio and a first calibration relationship between modulation ratio and oxygen saturation;
   estimate a second channel physiological characteristic value using the second modulation ratio and a second calibration relationship between modulation ratio and oxygen saturation, different from the first calibration relationship; and
   determine one or more physiological characteristics using the first channel physiological characteristic value and the second channel physiological characteristic value.

2. The device of claim 1, wherein:
the first channel has the first expected distribution of light paths due to a first separation distance between a first light emitter and a first light detector of the first channel; and
the second channel has the second expected distribution of light paths due to a second separation distance between a second light emitter and a second light detector of the second channel, different from the first separation distance.

3. The device of claim 1, wherein:
the first channel has the first expected distribution of light paths due to a first separation distance between a light emitting component within a first light emitter and a first light detector of the first channel or due to a first angle of the light emitting component within the first light emitter;
the second channel has the second expected distribution of light paths due to a second separation distance between a light emitting component within a second light emitter and a second light detector of the second channel or due to a second angle of the light emitting component within a second light emitter; and
the first separation distance is different from the second separation distance or the first angle is different from the second angle.

4. The device of claim 1, wherein:
the first channel has the first expected distribution of light paths due to a first wavelength of a light emitting component of a first light emitter of the first channel; and
the second channel has the second expected distribution of light paths due to a second wavelength of a light emitting component of a second light emitter of the second channel different from the first wavelength.

5. The device of claim 1, wherein a third channel of the plurality of channels has the first expected distribution of light paths and a fourth channel of the plurality of channels has the second expected distribution of light paths, and wherein the processor is further programmed to:
   determine a third modulation ratio for the third channel and a fourth modulation ratio for the fourth channel;
   estimate a third channel physiological characteristic value using the third modulation ratio and the first calibration relationship between modulation ratio and oxygen saturation;
   estimate a fourth channel physiological characteristic value using the fourth modulation ratio and the second calibration relationship between modulation ratio and oxygen saturation; and
   compute the one or more physiological characteristics using the first channel physiological characteristic value, the second channel physiological characteristic value, the third channel physiological characteristic value, and the fourth channel physiological characteristic value.

6. The device of claim 5, wherein:
the first channel and the third channel have the first expected distribution of light paths due to a first separation distance between a first light emitter and a first light detector of the first channel and the first separation distance between a third light emitter and a third light detector of the third channel; and
the second channel and the fourth channel have the second expected distribution of light paths due to a second separation distance, different from the first separation distance, between a second light emitter and a second light detector of the second channel and the second separation distance between a fourth light emitter and a fourth light detector of the fourth channel.

7. The device of claim 1, wherein a third channel of the plurality of channels has the first expected distribution of light paths, and wherein the processor is further programmed to:
   determine a third modulation ratio for the third channel;
   estimate a third channel physiological characteristic value using the third modulation ratio and the first calibration relationship between modulation ratio and oxygen saturation; and
   compute the one or more physiological characteristics using the first channel physiological characteristic value, the second channel physiological characteristic value, and the third channel physiological characteristic value.

8. The device of claim 1, wherein a third channel of the plurality of channels has the first expected distribution of light paths and a fourth channel of the plurality of channels has the second expected distribution of light paths, and wherein the processor is further programmed to:
   determine a third modulation ratio for the third channel and a fourth modulation ratio for the fourth channel;
   estimate a third channel physiological characteristic value using the third modulation ratio and a third calibration relationship between modulation ratio and oxygen saturation, different from the first calibration relationship and the second calibration relationship;
   estimate a fourth channel physiological characteristic value using the fourth modulation ratio and a fourth calibration relationship between modulation ratio and oxygen saturation, different from the first calibration relationship, the second calibration relationship, and the third calibration relationship; and
   compute the one or more physiological characteristics using the first channel physiological characteristic value, the second channel physiological characteristic value, the third channel physiological characteristic value, and the fourth channel physiological characteristic value.

9. The device of claim 1, wherein the second calibration relationship between modulation ratio and oxygen saturation is generated by applying a distance-dependent correction factor to the first calibration relationship between modulation ratio and oxygen saturation.

10. The device of claim 1, wherein the first calibration relationship or the second calibration relationship includes a wavelength-dependent correction factor.

11. The device of claim 1, wherein:
the first channel physiological characteristic value is a first cSpO2;
the second channel physiological characteristic value is a second cSpO2; and
the one or more physiological characteristics include perfusion indices, perfusion index ratios, and/or an SpO2 estimate.

12. A method comprising:
at a device including an optical sensor configured to measure physiological signals from a plurality of channels and a processor coupled to the optical sensor:
determining a first modulation ratio for a first channel of the optical sensor and a second modulation ratio for a second channel of the optical sensor, wherein the first channel has a first expected distribution of light paths and the second channel has a second expected distribution of light paths different from the first expected distribution of light paths;
estimating a first channel physiological characteristic value using the first modulation ratio and a first calibration relationship between modulation ratio and oxygen saturation;
estimating a second channel physiological characteristic value using the second modulation ratio and a second calibration relationship between modulation ratio and oxygen saturation, different from the first calibration relationship; and
determining one or more physiological characteristics using the first channel physiological characteristic value and the second channel physiological characteristic value.

13. The method of claim 12, wherein:
the first channel has the first expected distribution of light paths due to a first separation distance between a first light emitter and a first light detector of the first channel; and
the second channel has the second expected distribution of light paths due to a second separation distance between a second light emitter and a second light detector of the second channel, different from the first separation distance.

14. The method of claim 12, wherein:
the first channel has the first expected distribution of light paths due to a first separation distance between a light emitting component within a first light emitter and a first light detector of the first channel or due to a first angle of the light emitting component within the first light emitter;
the second channel has the second expected distribution of light paths due to a second separation distance between a light emitting component within a second light emitter and a second light detector of the second channel or due to a second angle of the light emitting component within a second light emitter; and the first separation distance is different from the second separation distance or the first angle is different from the second angle.

15. The method of claim 12, wherein:
the first channel has the first expected distribution of light paths due to a first wavelength of a light emitting component of a first light emitter of the first channel; and
the second channel has the second expected distribution of light paths due to a second wavelength of a light emitting component of a second light emitter of the second channel different from the first wavelength.

16. The method of claim 12, wherein a third channel of the optical sensor has the first expected distribution of light paths and a fourth channel of the plurality of channels has the second expected distribution of light paths, the method further comprising:
determining a third modulation ratio for the third channel and a fourth modulation ratio for the fourth channel;
estimating a third channel physiological characteristic value using the third modulation ratio and the first calibration relationship between modulation ratio and oxygen saturation;
estimating a fourth channel physiological characteristic value using the fourth modulation ratio and the second calibration relationship between modulation ratio and oxygen saturation; and
computing the one or more physiological characteristics using the first channel physiological characteristic value, the second channel physiological characteristic value, the third channel physiological characteristic value, and the fourth channel physiological characteristic value.

17. The method of claim 16, wherein:
the first channel and the third channel have the first expected distribution of light paths due to a first separation distance between a first light emitter and a first light detector of the first channel and the first separation distance between a third light emitter and a third light detector of the third channel; and
the second channel and the fourth channel have the second expected distribution of light paths due to a second separation distance, different from the first separation distance, between a second light emitter and a second light detector of the second channel and the second separation distance between a fourth light emitter and a fourth light detector of the fourth channel.

18. The method of claim 12, wherein a third channel of the optical sensor has the first expected distribution of light paths, and the method further comprising:
determining a third modulation ratio for the third channel;
estimating a third channel physiological characteristic value using the third modulation ratio and the first calibration relationship between modulation ratio and oxygen saturation; and
computing the one or more physiological characteristics using the first channel physiological characteristic value, the second channel physiological characteristic value, and the third channel physiological characteristic value.

19. The method of claim 12, wherein a third channel of the optical sensor has the first expected distribution of light paths and a fourth channel of the optical sensor has the second expected distribution of light paths, the method further comprising:
determining a third modulation ratio for the third channel and a fourth modulation ratio for the fourth channel;

estimating a third channel physiological characteristic value using the third modulation ratio and a third calibration relationship between modulation ratio and oxygen saturation, different from the first calibration relationship and the second calibration relationship;

estimating a fourth channel physiological characteristic value using the fourth modulation ratio and a fourth calibration relationship between modulation ratio and oxygen saturation, different from the first calibration relationship, the second calibration relationship, and the third calibration relationship; and computing the one or more physiological characteristics using the first channel physiological characteristic value, the second channel physiological characteristic value, the third channel physiological characteristic value, and the fourth channel physiological characteristic value.

20. The method of claim 12, wherein the second calibration relationship between modulation ratio and oxygen saturation is generated by applying a distance-dependent correction factor to the first calibration relationship between modulation ratio and oxygen saturation.

21. The method of claim 12, wherein the first calibration relationship or the second calibration relationship includes a wavelength-dependent correction factor.

22. The method of claim 12, wherein:
the first channel physiological characteristic value is a first cSpO2;
the second channel physiological characteristic value is a second cSpO2; and
the one or more physiological characteristics include perfusion indices, perfusion index ratios, and/or an SpO2 estimate.

23. A device comprising:
an optical sensor including a plurality of channels and configured to measure physiological signals from the plurality of channels, wherein the plurality of channels include channels with asymmetric distances; and
a processor coupled to the optical sensor and programmed to:
determine one or more physiological characteristics using a plurality of modulation ratios from the plurality of channels and using distance-dependent calibration relationships between modulation ratio and oxygen saturation.

* * * * *